United States Patent
Savran et al.

(10) Patent No.: US 9,850,478 B2
(45) Date of Patent: Dec. 26, 2017

(54) COMPOSITES MATERIAL WITH SUSPENDED PARTICLES AND METHOD OF USING THE SAME

(71) Applicant: Purdue Research Foundation, West Lafayette, IN (US)

(72) Inventors: Cagri A. Savran, West Lafayette, IN (US); Bin-Da Chan, West Lafayette, IN (US); Richard Lee Gieseck, III, Columbus, OH (US)

(73) Assignee: Purdue Research Foundation, West Lafayette, IN (US)

( * ) Notice: Subject to any disclaimer, the term of this patent is extended or adjusted under 35 U.S.C. 154(b) by 180 days.

(21) Appl. No.: 14/824,577

(22) Filed: Aug. 12, 2015

(65) Prior Publication Data

US 2016/0046924 A1    Feb. 18, 2016

Related U.S. Application Data

(60) Provisional application No. 62/036,440, filed on Aug. 12, 2014.

(51) Int. Cl.
*B01J 20/22* (2006.01)
*C12N 11/04* (2006.01)
*B81B 1/00* (2006.01)

(52) U.S. Cl.
CPC ............... *C12N 11/04* (2013.01); *B01J 20/22* (2013.01); *B81B 1/00* (2013.01)

(58) Field of Classification Search
CPC .................................. C12N 11/04; C12Q 1/18
USPC ............................................... 427/2.1; 435/32
See application file for complete search history.

(56) References Cited

U.S. PATENT DOCUMENTS

2007/0054349 A1*  3/2007  Hickey ............... B01F 13/0059
                                                                    435/32

* cited by examiner

*Primary Examiner* — Dah-Wei D Yuan
*Assistant Examiner* — Andrew Bowman
(74) *Attorney, Agent, or Firm* — Piroozi-IP, LLC (57) ABSTRACT

An intermediate composite capable of transferring a biological or chemical material to be patterned on a surface. The intermediate composite includes a hydrogel, and particles suspended in the hydrogel, generating a particle-gel composite (composite), the composite is configured to absorb a biological or chemical material (agent), and further configured to deposit the agent when the composite is positioned proximate to a surface on which the agent is to be deposited.

10 Claims, 8 Drawing Sheets

COMPOSITES MATERIAL WITH SUSPENDED PARTICLES AND METHOD OF USING THE SAME

CROSS-REFERENCE TO RELATED APPLICATIONS

The present patent application is related to and claims the priority benefit of U.S. Provisional Patent Application Ser. No. 62/036,440, filed Aug. 12, 2014, the contents of which is hereby incorporated by reference in its entirety into this disclosure.

TECHNICAL FIELD

The present invention generally relates to micro-patterning and particularly to micro-patterning a surface to functionalize the surface.

BACKGROUND

This section introduces aspects that may help facilitate a better understanding of the disclosure. Accordingly, these statements are to be read in this light and are not to be understood as admissions about what is or is not prior art.

Functionalizing solid flat surfaces or micro/nano sensor surfaces is a widely used procedure in many fields including biology, chemistry, medicine, and biomedical engineering. This procedure is usually performed by pipetting liquids onto an area larger than the intended area (in order to ensure sufficient coverage). Patterning of surfaces in order to result in gradients where the deposited pattern changes (i.e., in amount or in a particular dimension) has been used in diverse applications ranging from bio sensing to cell culture systems. Several methods have been employed to create such gradients including diffusion-based microfluidics, laser desorption, and photochemistry. However, such methodologies often require complex equipment and harsh treatments which prevent the widespread use of gradient patterning.

Techniques such as micro-contact printing do exist but they require a "stamp" be prepared beforehand. The user cannot change the stamp pattern. If the user decides that a new pattern is needed, the user has to make a new stamp with the desired new pattern.

Therefore, there is an unmet need for a novel approach that can selectively and robustly functionalize a surface by depositing biological or chemical traces on the surface.

SUMMARY

An intermediate composite capable of transferring a biological or chemical material to be patterned on a surface is disclosed. The intermediate composite includes a hydrogel, and particles suspended in the hydrogel, generating a particle-gel composite (composite), the composite is configured to absorb a biological or chemical material (agent), and further configured to deposit the agent when the composite is positioned proximate to a surface on which the agent is to be deposited.

A method of depositing biomolecules or chemical material on a surface is also disclosed. The method includes suspending spores in a hydrogel, generating a hydrogel-spore composite (intermediate composite). The method also includes embedding biomolecule or chemical material (agent) into the intermediate composite thereby allowing absorption of the agent by the spores generating a composite (Composite). In addition, the method includes micro-manipulating the Composite proximate to a surface resulting in deposition of the agent on the surface.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

A novel approach that can selectively and robustly functionalize a surface by depositing biological or chemical traces on the surface is disclosed. The approach includes a patterning strategy based upon a spore-hydrogel composite material, e.g., by suspending *Bacillus subtilis* (also referred to as *B. subtilis*) spores within a humidity sensitive hydrogel. The spore-hydrogel composite provides the capability to absorb chemicals and biological agents (generally referred to as agent), collectively (i.e., spore-hydrogel composite and agent) referred to as Composite, thereby generating a microenvironment that can be manipulated by a micromanipulator in order to deposit the absorbed agent onto a surface. Deposition on to the surfaces can be carried out in a variety of user-defined patterns. For example, a user can functionalize a surface in a zig-zag, circular or other more complicated patterns. One can engineer the properties of the Composite by controlling the amount and the type of the spores introduced into the Composite. Moreover, by controlling the humidity in the environment, the user can also control the amount of agent that is released by the Composite. Hence, it is possible to generate user-defined patterns with user-defined concentrations. Controlling the humidity level is one example of controlling the chemical release.

It should be understood that the approach described herein is not limited to *B. subtilis*. Other spores can also be employed. Further, the approach is not intended to be limited to spores. Materials other than spores can be employed, such as spheres, cells, micro particles or nano particles that have organic or inorganic content.

*Bacillus subtilis* is a commonly found bacterium usually recovered from water, soil, air, and decomposing plant residue. The bacterium produces an endospore that allows it to endure extreme conditions of heat and desiccation in the environment. *B. subtilis* produces a variety of proteases and other enzymes that enable it to degrade a variety of natural substrates and contribute to nutrient cycling. However, under most conditions the organism is not biologically active but exists in the spore form. *B. subtilisis* is considered a benign organism as it does not possess traits that cause disease.

A Hydrogels is a network of polymer chains that are generally hydrophilic, sometimes found as a colloidal gel in which water is the dispersion medium. Hydrogels are highly absorbent (they can contain over 90% water) natural or synthetic polymeric networks. Hydrogels also possess a degree of flexibility very similar to natural tissue, due to their significant water content.

*B. subtilis* can swell and absorb water from humid environments in addition to acting as a micro-carrier when brought into coupling with a biological/chemical agent. In the present disclosure, the ability of *B. subtilis* to act as such a carrier is demonstrated by loading *B. subtilis* spores that are embedded in a hydrogel forming the hydrogel-spore composite, altogether including the dye forming the Composite. For example, by saturating spores with a fluorescent dye and subjecting the Composite to various humidity levels, the concentration of dye released from the hydrogel surface can be controlled. In this disclosure it is demonstrated therefore that the carrier (*B. subtilis* spores in the hydrogel-spore composite) can be used to engineer the concentration of the agent within the hydrogel-spore composite, and hence this approach can be exploited as an additional parameter to control the agent release process. The fluorescent dye used here is an example of a material that can be used. As discussed above, it should be appreciated that the use of the dye is used inter alia to demonstrate the effectiveness of the novel arrangement according the present disclosure, and that the dye can be replaced with a variety of agents such as biomolecules including proteins, DNA, RNA, small molecules, peptides, ions, salts, sugars, cells, and pathogens including viruses and bacteria.

Figures 1A, 1B:
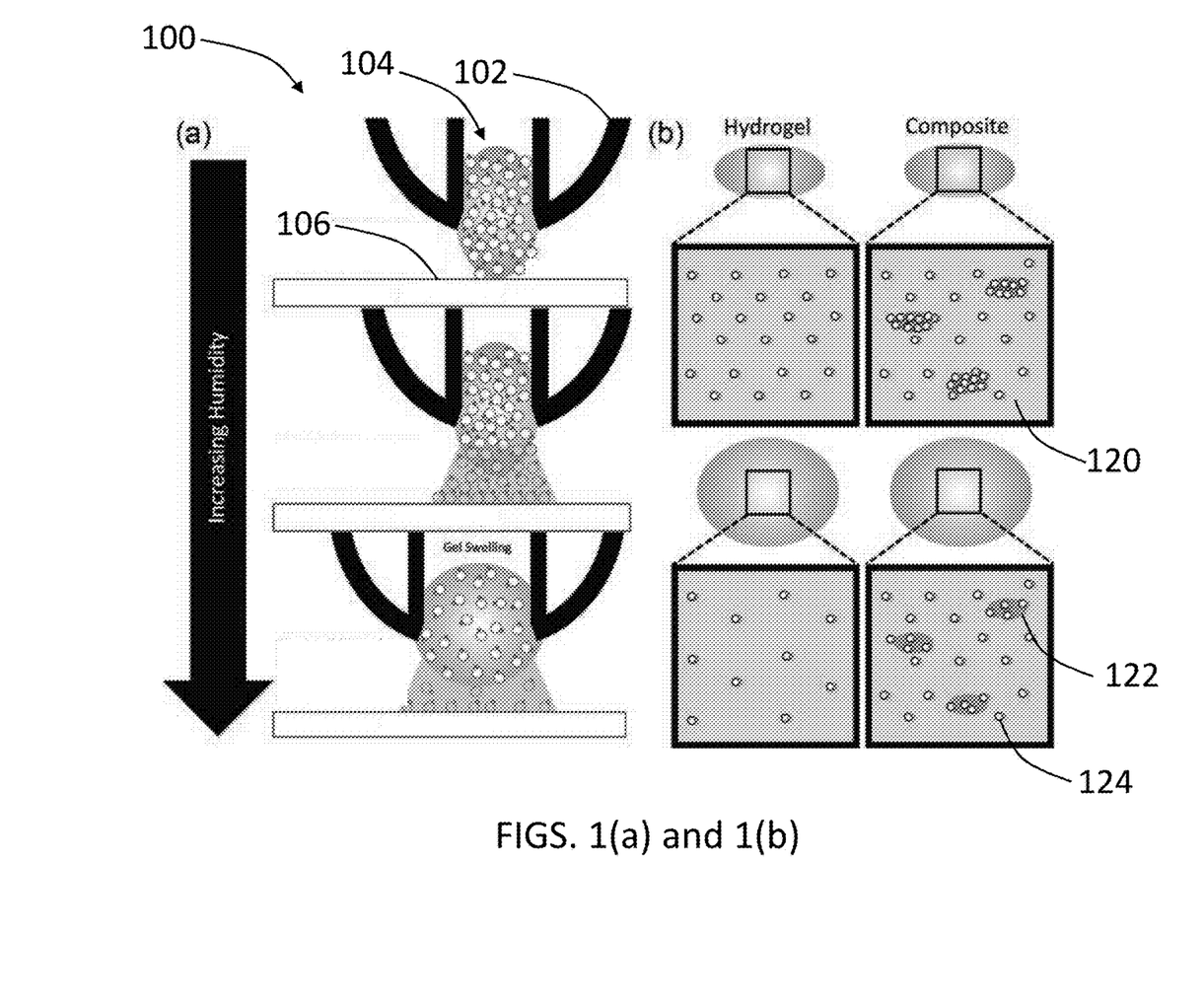
FIG. 1(a) is a schematic illustration of a patterning procedure according to the present disclosure that is used to generate user-defined surface concentrations.
FIG. 1(b) is a schematic illustration representing ability of negatively charged spores to bind to a positively charged agent.
Figure 1C:
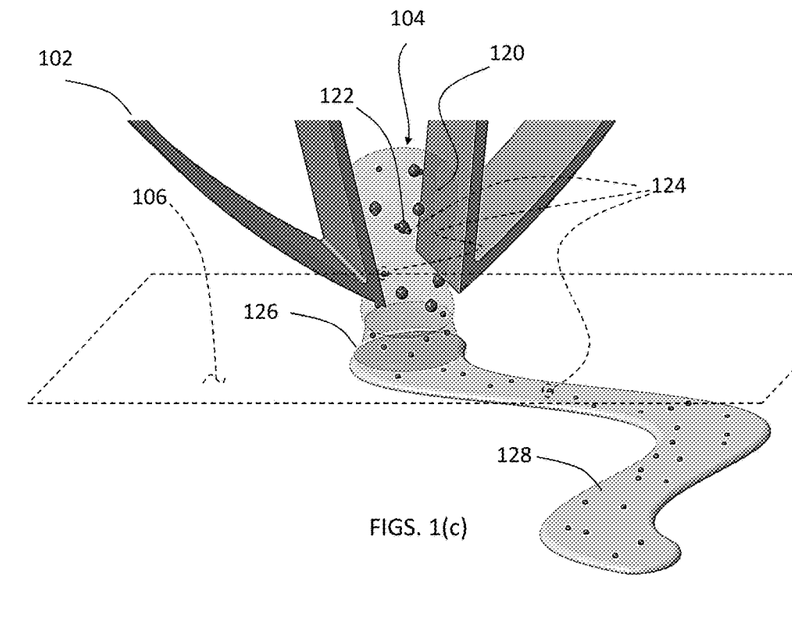
FIG. 1(c) is a schematic illustration of a micromanipulator depositing an agent on a surface according to the present disclosure.

FIG. 1(*a*) is a schematic illustration of a patterning procedure 100 according to the present disclosure to generate user-defined surface concentrations of an agent on a surface. In an exemplary embodiment, a micromanipulator 102 is used to handle Composite 104 and place the Composite 104 near a surface 106 according to a user-defined pattern. The Composite 104 as shown in FIGS. 1(*a*) and 1(*c*) includes a hydrogel 120, spores 122 dispersed throughout the hydrogel 120 at a predefined concentration, and agent which includes agent molecules identified as 124 in FIG. 1(*c*) and agent liquid identified as 128 in FIG. 1(*c*).

Referring back to FIG. 1(*a*), the concept of agent transfer is depicted. When the agent (including agent molecules 124 and agent liquid (see FIG. 1(*c*)) has already been introduced to the hydrogel-spore composite generating the Composite 104, the agent molecules 124 (see FIG. 1(*c*)) are carried by the spores 122 as well as by the hydrogel 120 which also carries the agent liquid 128. The agent including the agent molecules 124 and agent liquid 128 is transferred to the surface 106 when the Composite 104 is brought proximate to the surface 106. The mechanism of transfer is typically based on formation of a meniscus 126 (see FIG. 1(*c*)) when the micromanipulator 102 brings the Composite 104 near the surface 106 and when the humidity levels are at an appropriate level. At low humidity levels, the meniscus 126 does not form at the Composite 104 and surface 106 interface leading to low levels of agent transfer (as shown in the upper panel of FIG. (1*a*)). At mid-range humidity levels, a liquid meniscus forms allowing transfer of the agent (containing agent molecules 124 and agent fluid 128) on to the surface 106 (middle panel of FIG. 1(*a*)). As the humidity increases further, the hydrogel 120 absorbs more water and swells (bottom panel of FIG. 1(*a*)); thus, diluting the internal concentration of the agent (including the agent molecules 124 and the agent liquid 128) inside the Composite 104, and thus decreasing the concentration of the agent that is transferred to the surface 106.

To further improve the concentration of the agent within the Composite 104, the agent molecules 124 can be electrically charged with a charge opposite to the charge of the spores 122. FIG. 1(*b*) is a schematic illustration of the ability of negatively charged spores 122 to bind to positively charged agent molecules 124, thus increasing the internal concentration of the agent molecules 124. The left panels of FIG. 1(*b*) depict the hydrogel with spores therein. The right panels of FIG. 1(*b*) depict the Composite 104 (i.e., hydrogel 120, spores 122, and the agent (i.e., the agent molecules 124 and the agent liquid 128)). In the top panels of FIG. 1(*b*), the hydrogel 120 is shown in a mid-level humidity thereby allowing a high concentration of spores 122 and thereby a higher concentration of the agent molecules 124. With the agent molecules 124 positively charged, a high concentration of the agent molecules 124 can be associated with the spores 122 and the hydrogel 120. In the bottom panels of FIG. 1(*b*), the hydrogel 120 is shown in a high-level humidity thereby resulting in a low concentration of spores 122 (bottom-left panel of FIG. 1(*b*)) and spores 122 and agent molecules 124 together (bottom-right panel of FIG. 1(*b*)). In other embodiments of this disclosure, the spores can be replaced with other suspended particles of a material and with a certain charge that attracts dyes or other chemicals of the opposite charge. Alternatively, spores can be replaced with other particles that retain agents to be released by ways other than electrostatic interaction.

It should be appreciated that the direct use of spores to pattern on surfaces proves difficult due to the brittle nature of spore aggregates and the small size of spores (approximately 1 μm). The arrangement according to the present disclosure address this problem by suspending the spores in a stimuli-responsive hydrogel to improve the structural integrity of the spores while maintaining access to environmental humidity. In addition, the large size of the hydrogel construct (50-100 μm) facilitates manual manipulation using micromanipulators, thus allowing easy, user-controlled patterning using the Composite 104.

Figure 2:
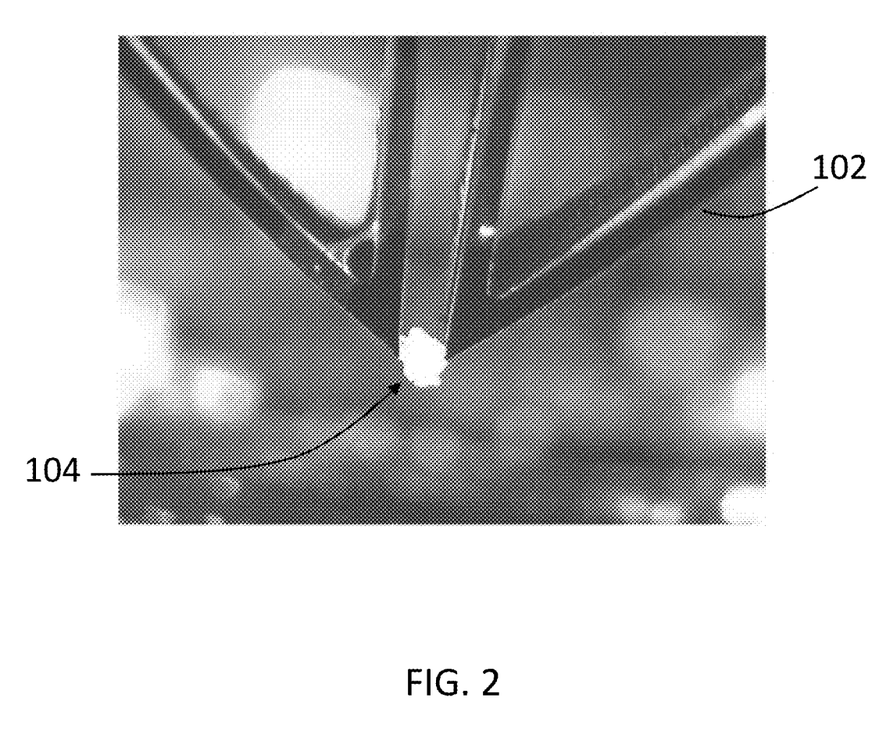
FIG. 2 is a micrograph of a composite material being manipulated by a mechanical micro-tweezers.

FIG. 2 is a micrograph of the Composite 104 being manipulated by the mechanical micromanipulator 102. The micromanipulator 102 allows for patterning size selection through grasping different sizes of Composite 104; in addition, the micromanipulator 102 gives the user precise spatiotemporal control over the patterning.

The hydrogel-spore composites were prepared by drying either 0.1 ml or 0.2 ml of *B. subtilis* spores, $10^7$ CFU (MESA LABS) (the term CFU is generally used to mean colony forming units) and suspending the resultant spore powder into 0.9 ml of 25.9 mg acrylamide (SIGMA-ALDRICH) containing 75.2 μl ulmethacrylic acid (SIGMA-ALDRICH, distilled to remove inhibitor), 12.2 mg N,N_-methylenebisacrylamide (Polysciences Inc.), and 75 μl N,N,N_,N_- tetramethylethylenediamine (SIGMA-ALDRICH) dissolved in deionized (DI) water. Gelation was induced by adding the solution into a 0.1 ml aqueous solution of 0.35 M ammonium persulfate and subsequently vortexing to ensure uniformity in spore distribution. A negative charge control was made by pipetting 0.5 µl poly(lactic-co-glycolic acid) (PLGA) microspheres (1% aqueous suspension of 1 µm microspheres, PHOSPHOREX INC.) into the solution prior to gelation in order to mimic the charge and size of spores within the gel.

Figure 3:
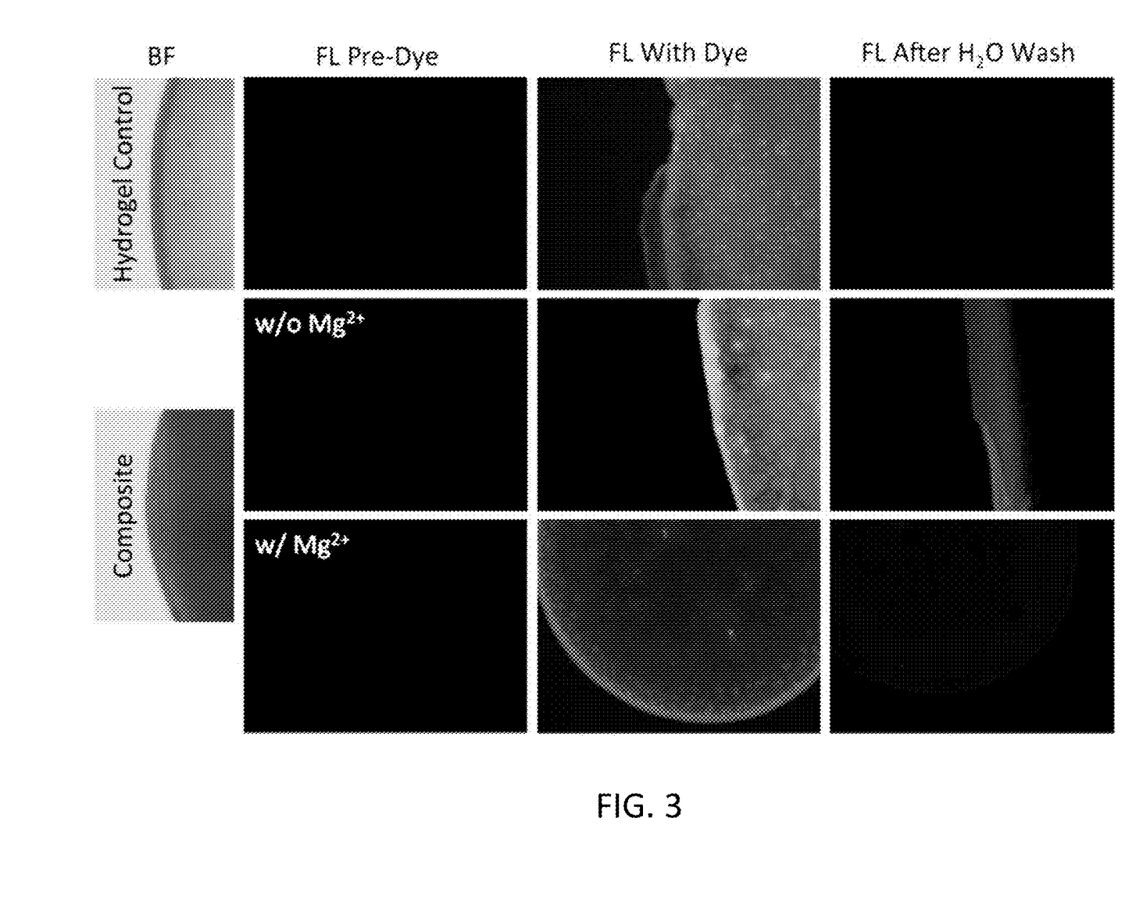
FIG. 3 is a micrograph showing bright field and fluorescent images of a hydrogel, and a hydrogel-spore composite when they are exposed to a dye.
Figure 4:
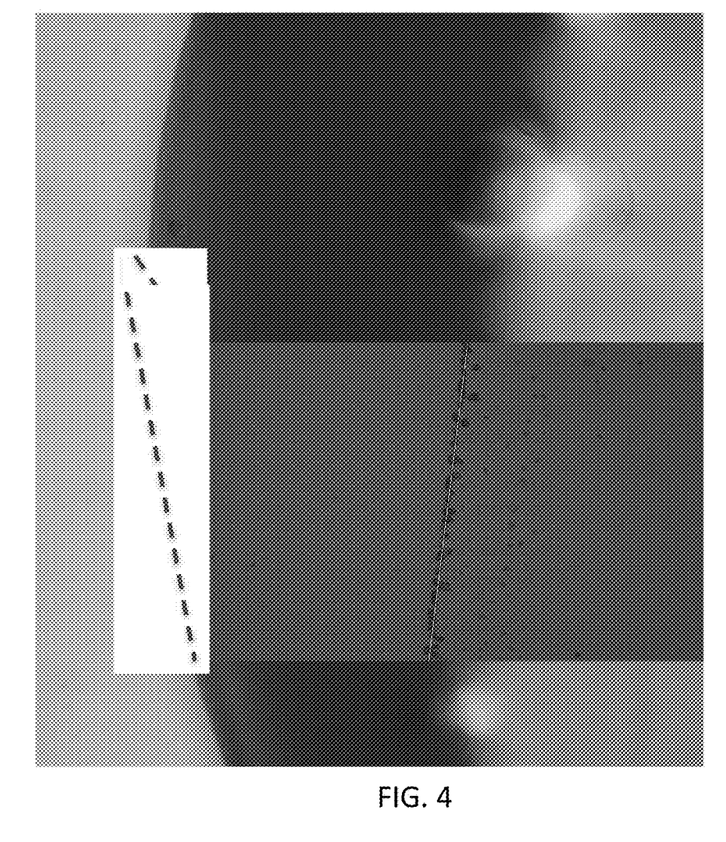
FIG. 4 is a micrograph depicting a hydrogel-spore composite according to the present disclosure, showing that the spores may tend to cluster near the surface of the hydrogel due to convective forces.
Figure 5:
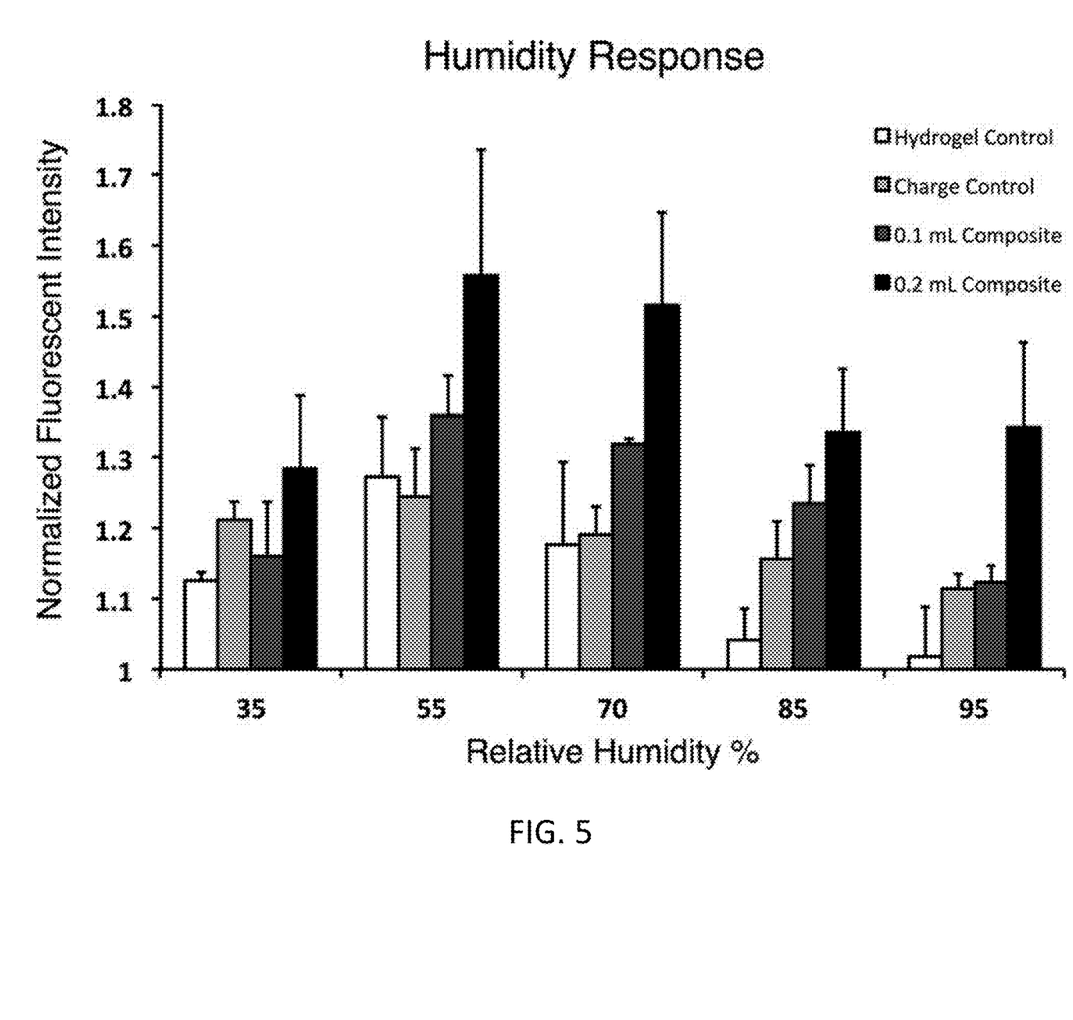
FIG. 5 is a plot of normalized fluorescent intensity vs. relative humidity obtained from a humidity response experiment.
Figure 6:
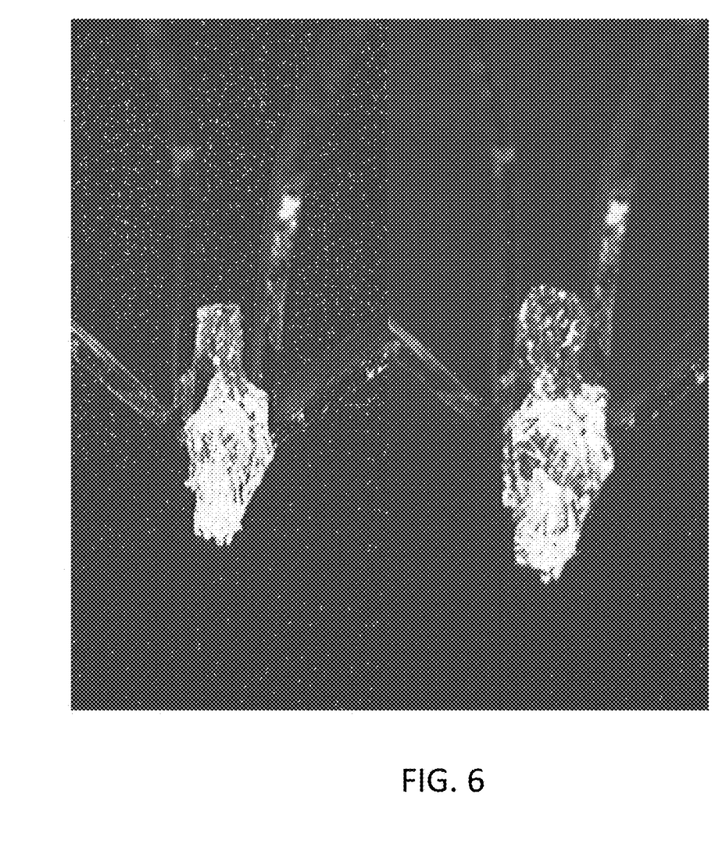
FIG. 6 is a micrograph showing volumetric changes in fluorescein isothiocyanate (FITC)-loaded composite gel due to increase in humidity.

The binding and retention of avidin-fluorescein isothiocyanate (FITC) was verified by plating the hydrogel Composites on a glass slide, saturating the hydrogel with avidin-FITC (SIGMA-ALDRICH), and triple rinsing with running deionized water for 5 min. FIG. 3 is a micrograph showing bright field and fluorescent images of hydrogel-only control, and loaded hydrogel-spore composites (i.e., Composites). In FIG. 3, the top row shows bright field and fluorescent micrographs of hydrogel control (left panel without any agent introduced, middle panel with dye agent introduced, and right panel representing the status after a wash with $H_2O$) while the bottom two rows show hydrogel-spore composites. The images in the left column correspond to a stage before the addition of avidin-FITC, the images in the middle column correspond to a stage after such addition, and the right column represents images after a 1-minute wash with water. These images demonstrate the binding of dye is at least partially charge dependent (difference between the middle row, particularly the right panel, and the bottom row, particularly the right panel). The gel constructs can be visualized as the dark area on the right-hand side of the bright field images.

Figure 7:
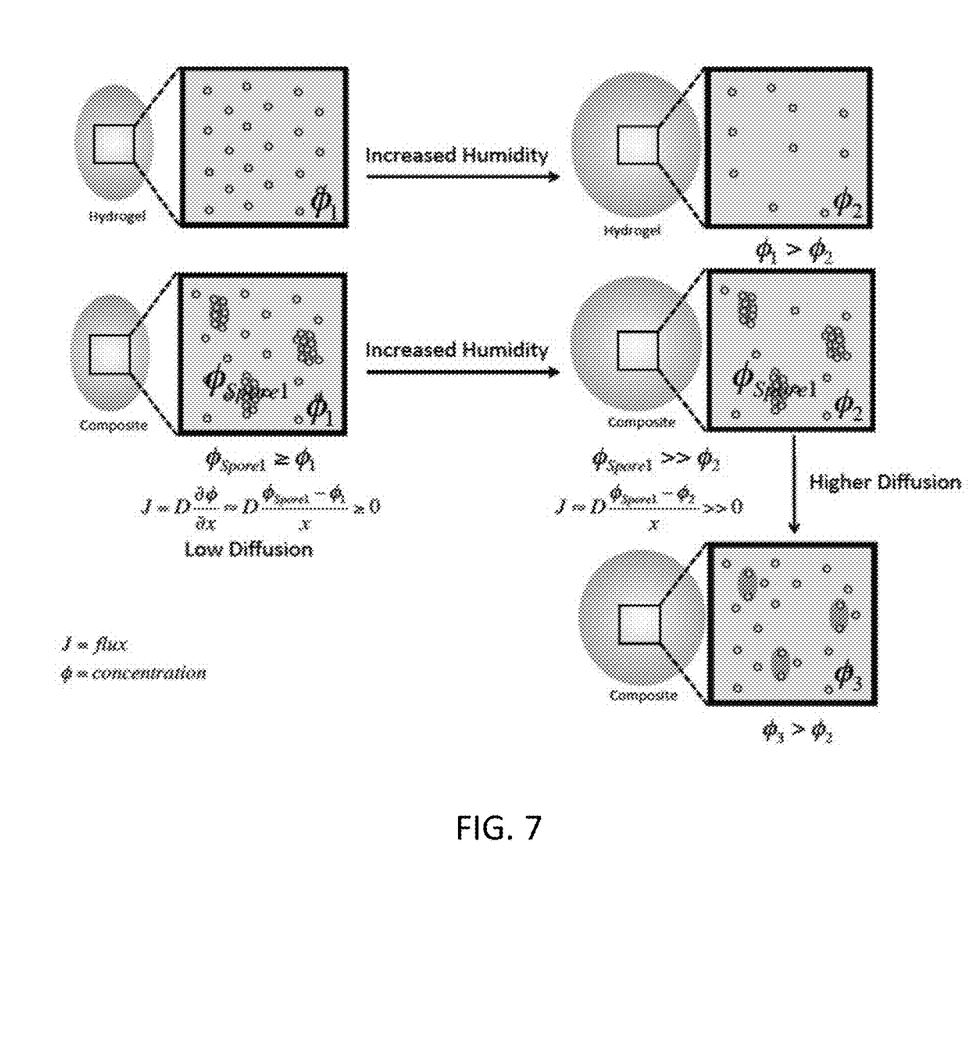
FIG. 7 is a schematic illustration of a model showing the mechanism by which spores can increase the concentration of chemical or biological agents inside the hydrogel.

FIG. 3 shows that the hydrogel-spore composite retains dye near the gel surface while a hydrogel-only control shows no significant retention of dye. When the hydrogel-spore composite was examined under bright field microscopy, spores were seen at very high concentrations near the surface of the gel. The concentration of spores decayed quickly from the surface to the hydrogel center. Since the hydrogel in this control experiment was synthesized directly on the surface of the glass slide, it is believed that the spores were pushed towards the hydrogel surface by convective forces and were subsequently set in place when gelation occurred. The high concentration of spores on the outer edge of the hydrogel-spore composite explains why fluorescence was seen only in the vicinity of the surface after rinsing. The water removed all dye from the hydrogel, except the dye protected by the spore coat. Another control was prepared by saturating the hydrogel-spore composite with a 1 M magnesium chloride solution in order to mask the negative surface charge of the spores. After the rinse, the magnesium control showed essentially no retention of dye, suggesting that the spore surface charge aids in the retention of the dye.

FIG. 4 is a micrograph depicting the hydrogel-spore composite, showing that the spores tend to cluster near the surface of the gel due to convective forces present during synthesis.

The humidity response of hydrogels with different concentrations of spores was characterized. Experiments were conducted with hydrogels devoid of spores (hydrogel control) and those that had negatively charged PLGA micro spheres instead of spores (charge control). A humidifier and a hygrometer were used to produce and measure the humidity in a chamber. First, hydrogel samples were saturated with avidin-FITC and allowed to dry. Small aliquots of each gel (approximately 50 μm in diameter) were grasped using a mechanical micromanipulator. The gel was placed in the humidity chamber for 2 min prior to patterning to acclimatize to the environment. However, the glass slide remained outside the chamber until immediately prior to patterning in order to avoid condensation on the surface. The gel was lowered until a meniscus formed on the glass slide, patterning a small circular spot on the surface. The gel sample was re-soaked fully for each humidity point to eliminate the effects of dye depletion from this experiment. The slide fluorescence profiles were immediately imaged to minimize photobleaching and were imported into a MATLAB algorithm for analysis. The intensity of each image was normalized to that of the background intensity of the glass slide and was averaged over the patterned area. This procedure was repeated for five different relative humidity levels, and three data points were obtained at each humidity level.

FIG. 5 is a plot of normalized fluorescent intensity vs. relative humidity obtained from the humidity response experiment described above in summary form. In FIG. 5, the error bars shown represent standard deviation of 3 experiments. FIG. 5 shows a large increase in intensity as the hydrogel is hydrated by increased relative humidity followed by a gradual decline as the concentration of the spores and thereby the concentration of the dye is decreased. Referring to FIG. 5, all experiments showed a rapid increase in fluorescent intensity followed by a gradual decline as the relative humidity was increased from 35% to 95%. The 0.2 ml hydrogel-spore composite showed the greatest increase in fluorescent intensity with 32% increase over that of the hydrogel control. Using unpaired, 2-tailed, heteroscedastic t-tests ($P<0.1$), significant difference was seen between the Composites and various controls. The 0.1 ml hydrogel-spore composite was statistically different from the charge control at 55% and 70% relative humidity and from the hydrogel control at 85% relative humidity. The 0.2 ml hydrogel-spore composite was statistically different from both controls for all relative humidity values except 35%. At 35% relative humidity, the dry gel-spore composite did not have enough moisture to form a meniscus to transfer dye to the surface, leading to low initial fluorescent intensity. However, at higher humidity levels, the hydrogel began to absorb ambient humidity leading to the formation of a meniscus and subsequent deposition of the fluorescent dye. As the humidity continued to increase, the gel significantly swelled with water, increasing in size and slowly diluting the concentration of dye within the gel, hence resulting in a decreased deposition of the fluorescent dye. FIG. 6 is a micrograph showing volumetric changes in the FITC-loaded Composite due to increase in humidity.

The level of fluorescent intensity deposited on the surface using the Composite is directly attributed to the ability of the Composite to bind higher concentrations of dye compared to the hydrogel and the charge control gel, thus creating a steeper gradient as the humidity is varied. The binding and retention experiment showed that charge plays a role in the ability of spores to bind higher levels of dye than hydrogel alone; however, the statistical difference from the charge control of the humidity response experiment suggests that the mechanism involves more than simple electrostatic interaction. Thus, there is a positive correlation between the peak concentration of patterned dye and the concentration of spores present in the Composite.

It should be noted that the amount of negatively charged surface area within the gel affects the rate at which surface concentration decreases as humidity increases. In the hydrogel control, as the humidity increases, the internal concentration decreases due to the increased volume of water. In the Composites, as the humidity increases, the internal concentration decreases as well. However, the dye bound to the charged surface has an increased diffusive flux due to the decreased concentration within the surrounding gel. This increases the diffusion from the spore to the surrounding gel, which attenuates the concentration lowering effects of increased humidity. FIG. 7 is a schematic illustration of a model showing the mechanism by which spores can attenuate the concentration lowering effects over mid-to-high humidity range compared to a hydrogel control.

As described above, a novel method of patterning biomolecules on a surface has been developed. The method includes suspending spores in a hydrogel forming a Composite, embedding a set of biomolecules desired to be deposited onto a surface into the Composite, and micromanipulating the Composite on the surface resulting in a deposition of the biomolecules on the surface. In one embodiment, the amount of biomolecules deposited is dependent on the humidity prevailing in the Composite. The humidity levels in the Composite can be controlled as described above. In one embodiment, for example, the spores can be *Bacillus Subtilis*. In other embodiments, spores other than *Bacillus subtilis*, such as *Bacillis anthracis* or other bacteria can be used to modify the properties of the hydrogel substrate. The spores or bacteria can be chosen based on the electrostatic, mechanical, optical, topographical, geometrical, material or chemical properties that may affect the type or the amount of the target dye or material that is to be released. In some embodiments of this disclosure, the use of spores can be totally replaced with the use of non-biological particles such as spheres, micro particles or nano particles that have organic or inorganic content including but not limited to magnetic particles, polystyrene particles, quantum dots that may attract and retain agents (e.g., biomolecules or chemicals to be released) by electrostatic, magnetic, steric, hydrophilic, hydrophobic, mechanical or chemical means. Further, in some embodiments, the material to be released to the surface can be biomolecules such as proteins, DNA, RNA, peptides, peptide nucleic acids, or small molecules, sugars, salts or ions. It should be further recognized, that in embodiments of this disclosure, the surface that receives the deposited material can be glass, silicon, silicon dioxide, indium tin oxide, polymeric, plastic, or metallic (meaning metal or alloy), including but not limited to gold, platinum, and other metals. The surface can be flat or irregular since the approach described in this disclosure allows depositing materials onto non-flat surfaces as well. For example, in one embodiment, the system can be used to deposit materials to the side of an object or selectively on the oblique planes of a prism like object. Further, it is envisioned that the surface can be that of a sensor or actuator or another device that needs the presence of certain chemicals or molecules or materials on it for operability or enhanced performance. Furthermore, while changes in humidity were accomplished by placing the spore-gel in a humidity chamber, selective humidity can be implemented on the surface by selectively applying the appropriate amount of vapor directly at the surface. While humidity was used as a stimulus in one of the embodiments described above to deposit and control the material, the stimulus that controls the material release need not be limited to humidity. For example, the release can be triggered or controlled by temperature, electric fields, magnetic fields, mechanical forces or by introduction of or exposure to other chemicals. It should be noted that such stimuli can be combined. For example, the stimuli of temperature and humidity can be used in combination to control the amount of material released from the Composite. In the approach described in this disclosure, the substrate material of the Composite may be different from a hydrogel and may include other gels, polymers or solids that can be manipulated by a pair of tweezers or similar manipulators. Also while a micromanipulator was discussed in the present disclosure for the purpose of manipulating the position of the Composite on to the surface, other devices and arrangements may be used to bring the Composite at a larger scale on to the surface.

While in this disclosure embodiments containing one Composite is described, it should be appreciated that multiple Composites can be employed in a patterning process of the type described in this disclosure. Further, the multiple Composites can contain varying chemistries or physical characteristics for the suspended particles. Furthermore, in utilizing multiple Composites and/or multiple chemistries or physical characteristics for the suspended particles, more than one stimulus can be utilized advantageously. The stimulus or stimuli can be chosen based on the effect of the stimulus or stimuli on the Composites and/or the suspended particles. Thus in a single patterning exercise, it is possible to combine a variety of Composites, a variety of suspended particles and a variety of stimuli. These possibilities can be exploited to control the rate of deposition and/or concentration gradients of the deposited materials.

It should be appreciated that the deposited agent, according to the present disclosure, can be deposited in a manner in which it generates a diffraction grating pattern. The agent can provide an affinity for binding to biological entities of particular variety, e.g., cells afflicted with a particular disease. The agent can then bind to those biological entities when a fluid containing those biological entities is passed over the deposited agent thereby generating a binding affinity to the agent. The diffraction grating pattern can then be used to quickly identify the bound biological entities using techniques known to a person having ordinary skill in the art.

It should be appreciated that the arrangement described herein for depositing the agent can be provided in an array. In other words, an array of micromanipulators can be grouped together to deposit various patterns of the agent on to the surface according to a user-defined pattern. In this embodiment, a larger pattern can be deposited in a shorter amount of time.

It should also be appreciated that the surface deposition of the agent can be accomplished on a combination of surface orientations, e.g., horizontal, vertical, angled, and any combination thereof.

Those having ordinary skill in the art will recognize that numerous modifications can be made to the specific implementations described above. The implementations should not be limited to the particular limitations described. Other implementations may be possible.

The invention claimed is:

1. A method of depositing biomolecules or chemical material on a surface, the method comprising:
suspending spores in a hydrogel, generating a hydrogel-spore composite (first composite);
embedding biomolecule or chemical material (agent) into the first composite thereby allowing absorption of the agent by the spores generating a second composite; and
micro-manipulating the second composite proximate to a surface resulting in deposition of the agent on the surface.

2. The method of claim 1, the spores are *Bacillus subtilis* spores.

3. The method of claim 2, wherein the hydrogel is humidity sensitive.

4. The method of claim 1, wherein the concentration of the agent deposited is humidity dependent.

5. The method of claim 4, wherein the humidity at the second composite can be varied from about 3.5% to about 95%.

6. The method of claim 1, wherein the step of micromanipulating is performed by a micromanipulator.

7. The method of claim 1, wherein more than one first composite is used, spores in each first composite configured to absorb a different embedded set of agents.

8. The method of claim 1, wherein the deposited agent result in a concentration gradient of the agent on the surface.

9. The method of claim 1, the agent is configured to be deposited on any combination of vertical and horizontal surfaces.

10. The method of claim 1, the agent is configured to be deposited according to a user-defined pattern.

\* \* \* \* \*